United States Patent [19]

Bryan

[11] 4,238,415

[45] Dec. 9, 1980

[54] PROCESS FOR PREPARING CYCLOALKANOLS AND CYCLOALKANONES

[75] Inventor: William O. Bryan, Augusta, Ga.

[73] Assignee: Stamicarbon, B.V., Geleen, Netherlands

[21] Appl. No.: 15,433

[22] Filed: Feb. 26, 1979

[30] Foreign Application Priority Data

Feb. 25, 1978 [NL] Netherlands .................. 7802125

[51] Int. Cl.$^3$ .............................. C07C 45/28
[52] U.S. Cl. .................... 568/342; 568/357
[58] Field of Search .............. 260/586 P; 568/357

[56] References Cited

FOREIGN PATENT DOCUMENTS 7207532 12/1972 Netherlands .................. 260/586 P Primary Examiner—Paul J. Killos
Attorney, Agent, or Firm—Cushman, Darby & Cushman

[57] ABSTRACT

An improved process for the preparation of cycloalkanols and cycloalkanones by the liquid phase oxidation of a cycloalkane having from 5 to 12 carbon atoms in the ring by means of a gas containing molecular oxygen to obtain an oxidation mixture containing cycloalkyl hydroperoxide and acids, and the subsequent decomposition of such cycloalkyl hydroperoxide to cycloalkanols and cycloalkanones. The decomposition is carried out by means of a metal salt in the presence of an aqueous solution of an alkali metal hydroxide. The improvement comprises a neutralization step wherein the acids contained in the oxidation mixture are first neutralized, forming a neutralized organic phase containing the cycloalkyl hydroperoxide, whereafter the neutralized organic phase is treated with a metal salt in the presence of an aqueous solution of an alkali metal hydroxide to decompose the cycloalkyl hydroperoxide and form an organic phase containing cycloalkanols and cycloalkanones.

12 Claims, 1 Drawing Figure

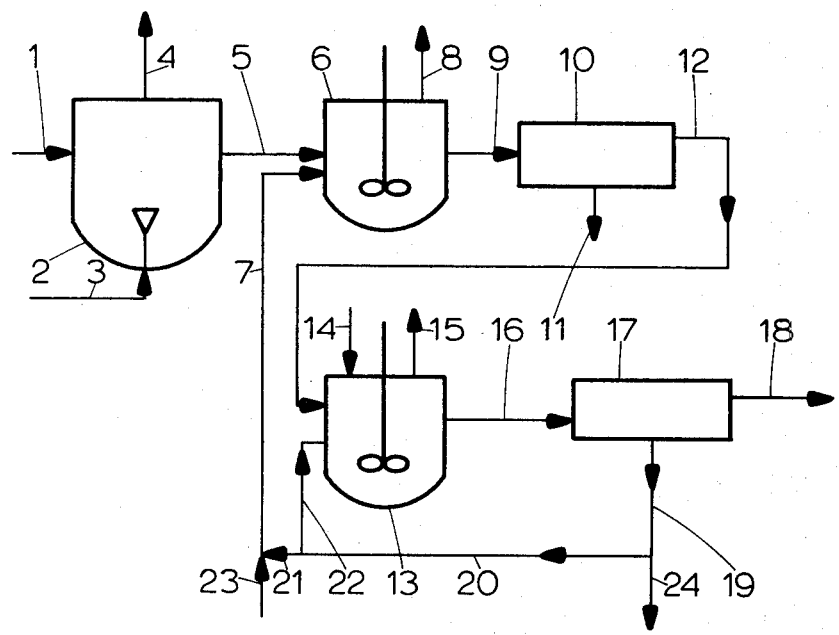

PROCESS FOR PREPARING CYCLOALKANOLS AND CYCLOALKANONES

BACKGROUND OF THE INVENTION

The present invention relates to a process for preparing cycloalkanols and cycloalkanones by the liquid phase oxidation of a cycloalkane, having from 5 to 12 carbon atoms in the ring, by means of a gas containing molecular oxygen. The oxidation mixture thus obtained, containing cycloalkyl hydroperoxide, is subsequently treated with a cycloalkyl hydroperoxide-decomposing salt in the presence of an aqueous solution of an alkali metal hydroxide to form cycloalkanols and cycloalkanones. A process of this type is known from British Patent Specification No. 1,382,849.

In this known process, the oxidation mixture containing the cycloalkyl hydroperoxide is treated with the alkaline solution simultaneously with, or subsequent to, the addition of the cycloalkyl hydroperoxide-decomposing metal salt, while the aqueous phase portion of the resulting reaction mixture is maintained at a pH of between 8 and 13, measured at 25° C. this process, however, has the disadvantage that the yield of cycloalkanols and cycloalkanones, based on the cycloalkane converted, is relatively low. Applicant has found that this yield can be enhanced by maintaining the aqueous phase portion of the reaction mixture at an extremely high pH, for instance corresponding with 0.5 N of free sodium hydroxide or more. However this requires a very high consumption of alkali, which in turn renders such a process economically unattractive.

It is therefore an object of this invention to provide an economically attractive process for the preparation of cycloalkanols and cycloalkanones having an increased yield as compared to the prior art processes. It is a further object of this invention to provide a process having increased yield of cycloalkanols and cycloalkanones, while at the same time minimizing the consumption of alkali.

DESCRIPTION OF THE INVENTION

Applicant has now found that a high yield of cycloalkanol and cycloalkanone can be achieved with a relatively low alkali consumption by neutralizing the acids present in the oxidation mixture as byproducts in a neutralizing step, prior to treating the mixture with the cycloalkyl hydroperoxide-decomposing metal salt in the presence of an alkaline solution in a subsequent decomposing step. Specifically, according to applicant's invention, cycloalkanols and cycloalkanones are prepared first by the liquid phase oxidation of a cycloalkane having 5 to 12 carbon atoms in the ring, by means of a gas containing molecular oxygen. The oxidation mixture thus obtained, containing cycloalkyl hydroperoxide and by-product acids, is then treated in a neutralization step wherein at least a portion of the acids present in the oxidation mixture are neutralized. The resulting neutralized organic phase containing cycloalkyl hydroperoxide is then treated in a subsequent decomposition step, in the presence of an aqueous solution of an alkaline metal hydroxide, with a metal salt which is capable of decomposing the cycloalkyl hydroperoxide to cycloalkanols and cycloalkanones. In this manner, an increased yield of cycloalkanols and cycloalkanones can be achieved while at the same time reducing the consumption of alkali.

The process is suitable for the preparation of cycloalkanols and cycloalkanones from cycloalkanes having 5 to 12 carbon atoms in the ring, most particularly cyclopentane, cyclododecane and especially cyclohexane. The invention will be described particularly with reference to the preparation of cyclohexanol and cyclohexanone from cyclohexane, but it should be understood that the process can be applied to such other cycloalkanes using comparable procedures.

The oxidation mixture resulting from the liquid phase oxidation of a cycloalkane contains, in addition to the cycloalkyl hydroperoxide, minor quantities of other peroxides such as the corresponding $\omega$-hydroperoxyalkane carboxylic acid and dicycloalkylperoxide, which for the sake of simplicity are to be understood as being included within the scope of the term "cycloalkyl hydroperoxide" as used herein. The oxidation takes place in a liquid phase, and the oxygen is provided by a molecular oxygen containing gas such as air or pure oxygen, or, for instance, nitrogen-oxygen mixtures of a composition differing from that of air such as mixtures of air and reactor off-gas. Suitable oxidation temperatures range between about 120° and 200° C., but preferably an operating temperature of between 140° and 180° C. is used. The operating pressure is not critical, but should be chosen such that a liquid phase is maintained throughout the oxidation. A pressure of between 400 and 5,000 kPa, for instance about 1,300 kPa, is suitable for this process. This oxidation results in a low rate of conversion of cycloalkanes supplied, for instance in the range of from about 1 to 12%.

Preferably the oxidation reaction is carried out in the absence of any substances which will promote the decomposition of the cycloalkyl hydroperoxide formed, such as compounds of transition metals. Thus it is preferable to carry out the oxidation in reactors having an inert inner wall made of, for example, passivated steel, aluminum, tantalium, glass, enamel or the like. In this manner the undesirable decomposition of cycloalkyl hydroperoxide under the oxidation conditions can be substantially avoided.

If desired however, small quantities of oxidation catalyst may be present during the oxidation, for instance not more than 10 ppm and preferably not more than 1 ppm of a transition metal in the form of a soluble salt. The preferred transition metal is cobalt, but chromium, manganese, iron, nickel or copper may be used as well. Cobalt naphthenate or cobalt 2-ethylhexanate have been found to be very suitable.

The oxidation reaction results in a pressurized, hot and rather diluted solution of cycloalkyl hydroperoxide in cycloalkane. Preferably this oxidation mixture is allowed to expand to a lower pressure, for instance to about 1,000 kPa, before further processing.

The oxidation mixture thus obtained is next treated in a neutralization step (a) wherein the byproduct acids present in the oxidation are neutralized. This can be accomplished by the addition of a neutralizing agent, preferably an aqueous solution of a hydroxide or carbonate of an alkali metal. This results in the formation of a neutralized organic phase containing the cycloalkyl hydroperoxide, and what is termed herein as a neutralization step aqueous phase. Preferably, the quantity of neutralizing agent added results in the neutralization step aqueous phase thus formed having a pH higher than 7° at 25° C., and preferably having a pH of between about 8 and 13. The neutralization step can take place over a wide range of temperatures, for instance from about 80° to 170° C., but preferably is carried out at a temperature of between about 130° to 160° C.

Suitable neutralizing agents include, for instance, sodium hydroxide, sodium carbonate, potassium hydroxide and potassium carbonate. A significant advantage of the process according to the present invention is that an alkali metal carbonate can be used as the base or neutralizing agent in the neutralization step, which step involves the largest consumption of base, and there is no need to use a costly alkali metal hydroxide.

In a preferred embodiment of the present process the decomposition step aqueous phase, obtained from decomposition step (b), can be used as at least a portion of the alkaline solution required in neutralization step (a). In this manner, the alkali consumption of the overall process can be even further reduced.

In another preferred embodiment, which can be used separately or in combination with the preceding preferred embodiment, an aqueous solution of alkali metal carbonate suitable for use as at least part of the neutralizing agent in the neutralization step, can be obtained through the combustion of various effluents derived from the process which contain alkali metal salts of carboxylic acids. A method for the preparation of such an aqueous solution is described in, for example, British Pat. No. 1,398,293. Suitable effluents for such combustion derived from the present process are the neutralization step aqueous phase from step (a) as well as the decomposition step aqueous phase from step (b). This embodiment permits an even further considerable reduction in the overall alkali consumption of the process.

Preferably, the neutralization step aqueous phase is separated from the neutralized organic phase from neutralization step (a) prior to introducing the neutralized organic phase into the peroxide decomposition stage (b). If desired, this separated neutralized organic phase may also be washed with water prior to its introduction into the peroxide decomposition step (b).

The cycloalkyl hydroperoxide decomposition is effected in decomposition step (b) by means of a cycloalkyl hydroperoxide-decomposing metal salt, which is normally a salt of a transition metal. Cobalt is preferred, although chromium, manganese, iron, nickel or copper, for instance, may also be used. Preferably the metal salt is water soluble, and sulphates and acetates are very suitable for this purpose.

The quantity of such metal salt should be generally in the range of between about 0.1 to 1,000 ppm by weight, calculated as the metal relative to the total weight of the aqueous phase present in the decomposition step. However larger quantities of metal salt may be utilized, but offer no advantage. Preferably 0.1 to 10 ppm of metal is used. The metal salt can be added efficiently to the reaction mixture in the form of an aqueous solution, possibly together with the alkali metal hydroxide. However it is also possible to add the metal to the reaction mixture in the form of an organic salt dissolved in an organic solvent, for instance the cycloalkane in question.

The peroxide decomposition treatment must be carried out in the presence of an alkali metal hydroxide. The quantity of alkali metal hydroxide is preferably chosen such that the hydroxyl ion concentration in the aqueous phase leaving the decomposition step is at least 0.1 N and is preferably at least 0.6 N. A hydroxyl ion concentration higher than 2 N may be used, but offers no advantage. In practice, a hydroxyl ion concentration of from 0.6 to 1 N is most suitable. Suitable alkali metal hydroxides for use in this decomposition step include, for instance, sodium hydroxide and potassium hydroxide.

In order to efficiently and effectively carry out the peroxide decomposition, the volume ratio between the aqueous phase and the organic phase in the decomposition step is preferably maintained at least about 0.02, and preferably between about 0.05 and 0.20. Higher volume ratios may be utilized, but they offer no particular advantage.

The decomposition of the cycloalkyl hydroperoxide may be carried out at a temperature in the range of, for instance, 80° to 170° C.

After completion of the decomposition reaction, the resulting decomposition step aqueous phase may be separated from the organic phase which contains the cycloalkanols and cycloalkanones. This organic phase can then be washed with water to remove salt residue, if desired, and the cyclohexanol and cyclohexanone can be isolated by means of distillation. The non-converted cycloalkane present in the organic phase can be returned to the oxidation reaction. As noted above, the aqueous phase resulting from the decomposition step can advantageously be recycled to the neutralization step.

It should be appreciated from the foregoing that the present process may be suitably carried out either batch-wise or as a continuous production process.

BRIEF DESCRIPTION OF THE DRAWING

The FIGURE schematically represents a suitable process configuration for carrying out a preferred embodiment of the present invention. This FIGURE will be discussed in detail in relation to the following examples.

DESCRIPTION OF PREFERRED EMBODIMENT

The numbers in the following examples are with reference to the FIGURE which represents a reaction diagram process configuration which can be utilized to carry out the process of the present invention. It should be understood that the diagram and examples are illustrative only, and other process configurations and parameters may be suitably utilized within the scope of the invention.

EXAMPLE I

This example utilizes an embodiment of the invention depicted in the FIGURE except that lines 22, 23 and 24 are not utilized.

In oxidation reactor 2, cyclohexane supplied through line 1 is oxidized in a liquid phase with air supplied through line 3 at a temperature of 165° and a pressure of 1,050 kPa. No metal salt catalyst is used. The rate of conversion of cyclohexane is 4.5 mol %, and the oxidation mixture contains 250 mmol of peroxide (calculated as cyclohexyl hydroperoxide) per kg. Cyclohexane is recovered from the off-gas discharged through line 4 in the usual manner, and is returned to the oxidation reaction. The residual off-gas is blown off.

The oxidation mixture is then supplied through line 5 to neutralization vessel 6, in which it is cooled through expansion to 145° C. The acids contained in the oxidation mixture are neutralized with the aqueous phase supplied through line 7 from phase separator 17 after decomposition reactor 13. Inert gas is not supplied to vessel 6. The off-gas discharged from neutralization vessel 6 through line 8 is condensed and separated into an aqueous phase (which is discharged) and an organic phase, which is returned as cyclohexane feed to oxidation reactor 2. The heat obtained from this condensation can be used elsewhere in the process.

After the neutralization step, the resulting liquid reaction mixture is supplied through line 9 to separator 10, where the two liquid phases are separated. The neutralization step aqueous phase is discharged through line 11 as waste water, from which sodium carbonate can be obtained through combustion if desired. The neutralized organic phase is supplied through line 12 to decomposition reactor 13, where it is thoroughly mixed with 5% by volume of an aqueous solution of sodium hydroxide containing 1 ppm $CoSO_4$, which is supplied through line 14. The concentration of the sodium hydroxide is chosen such that the hydroxyl ion concentration in the aqueous phase discharged from the neutralization step through line 11 is 0.01 N. The gas phase discharged through line 15 is treated in the manner as described for the gas phase in line 8. The liquid decomposition step reaction mixture goes through line 16 to separator 17, where it is separated into an aqueous phase, which goes through lines 19, 20, 21 and 7 to neutralization vessel 6, and an organic phase, which is discharged through line 18. This organic phase is processed into cyclohexanone and cyclohexanol through distillation by known methods. The non-converted cyclohexane recovered through this distillation is returned to oxidation reactor 2.

96% of the cyclohexyl hydroperoxide is converted, and the efficiency of the conversion to cyclohexanol plus cyclohexanone amounts to 94%. The quantity of free sodium hydroxide in the aqueous phase effluent from separator 10 is negligible.

EXAMPLE II

This example utilizes an embodiment of the present invention depicted in the FIGURE except that line 21 is not used.

An oxidation mixture obtained as in Example I is cooled through expansion to 145° C. and neutralized in neutralization vessel 6 with an excess of sodium carbonate such that the aqueous phase discharged through line 11 has a pH of 10. The sodium carbonate is supplied to neutralization vessel 6 through lines 23 and 7 in the form of an aqueous solution and in a quantity of at least 5% by volume relative to the oxidation mixture. After separation of the phases in separator 10, the neutralized organic phase is supplied to decomposition reactor 13, which is also supplied through line 14 with an aqueous sodium hydroxide solution containing 1 ppm $CoSO_4$.

In this embodiment of the process, the hydroxide consumption is very low. If a volume ratio of about 0.05 is to be maintained between the aqueous phase and the organic phase in the decomposition reactor, then the hydroxide would have to be supplied as a highly diluted solution, which is not very practical. This problem is solved by recycling sufficient aqueous phase effluent from separator 17 to decomposition reactor 13 through lines 19, 20 and 22, to achieve the desired aqueous phase/organic phase ratio. The sodium hydroxide concentration in line 14 is in the order of 20% by weight, but is controlled so that the hydroxyl ion concentration in the aqueous phase discharged through line 19 is maintained at 1 N.

The conversion of cyclohexyl hydroperoxide amounts to 96%, and the efficiency of conversion to cyclohexanol and cyclohexanone amounts to 94%.

The portion of the aqueous phase discharged through line 19 that is not returned to decomposition reactor 13, is, in this example, discharged through line 24. This effluent stream is relatively small and so the loss of hydroxide is low. Consumption of base can be further reduced by leading this discharged aqueous phase to neutralization vessel 6 through lines 21 and 7.

The aqueous phase effluents from lines 11 and 24 can be combusted in a known manner, giving sodium carbonate and/or sodium hydroxide. In a preferred embodiment of the process according to the invention, the conditions of this combustion are chosen so that the solid product obtained mainly consists of sodium carbonate, which is then dissolved in water, and the solution is supplied to neutralization vessel 6 through lines 23 and 7.

COMPARATIVE EXPERIMENT A

An oxidation mixture obtained in accordance with Example I is thoroughly mixed at 165° C. with 5% by volume of an aqueous sodium hydroxide solution, containing 1 ppm $CoSO_4$, in a continuous-flow ideally mixing reactor. The concentration of the sodium hydroxide has been chosen so that the hydroxyl ion concentration in the aqueous phase after separation is 0.1 N.

Only 65% of the cyclohexyl hydroperoxide has been converted, and the efficiency of conversion to cyclohexanol plus cyclohexanone is 87%.

COMPARATIVE EXPERIMENT B

Comparative Example A is repeated, but this time the concentration of sodium hydroxide has been chosen so that the hydroxyl ion concentration in the aqueous phase after phase separation is 0.6 N.

The conversion of cyclohexyl hydroperoxide is now 96%, and the efficiency of conversion to cyclohexanol and cyclohexanone is 94%.

The quantity of free sodium hydroxide in the aqueous phase effluent, however, is equivalent to 36 kg of sodium hydroxide per ton of cyclohexanone, which adversely affects the economic attractiveness of the process.

What is claimed is:

1. In a process for the preparation of cycloalkanols and cycloalkanones by the liquid phase oxidation of a cycloalkane having from 5 to 12 carbon atoms in the ring, by means of a gas containing molecular oxygen to obtain an oxidation mixture containing cycloalkyl hydroperoxide and acids, and thereafter treating said cycloalkyl hydroperoxide, in the presence of an aqueous solution of an alkali metal hydroxide, with a metal salt that causes decomposition of the cycloalkyl hydroperoxide to said cycloalkanols and cycloalkanones, the improvement comprising the combination of a neutralization step (a) wherein said oxidation mixture is treated with an aqueous solution of a neutralizing agent selected from the group consisting of an alkali metal hydroxide and an alkali metal carbonate to neutralize at least a portion of the acids contained therein thereby forming a neutralized organic phase containing said cycloalkyl hydroperoxide and a neutralization step aqueous phase, which aqueous phase is separated off, and a subsequent decomposition step (b) wherein said neutralized organic phase is treated with said metal salt in the presence of an aqueous solution of an alkali metal hydroxide thereby decomposing at least a portion of said cycloalkyl hydroperoxide and forming an organic phase containing said cycloalkanols and cycloalkanones and a decomposition step aqueous phase.

2. The process of claim 1 wherein said neutralizing agent added in step (a) is comprised at least in part of at least a portion of said decomposition step aqueous phase from step (b), resulting in the formation of said neutralized organic phase and a neutralization step aqueous phase.

3. The process of claims 1 or 2 wherein said neutralizing agent is added to step (a) in a sufficient quantity to result in the formation of said neutralization step aqueous phase having a pH higher than 7 at 25° C.

4. The process of claim 4 wherein said neutralization step aqueous phase has a pH of between about 8 and 13 at 25° C.

5. The process of claims 1 or 2 wherein said neutralizing agent added in step (a) is comprised at least in part of an aqueous solution of an alkali metal carbonate obtained by means of the combustion of at least a portion of said neutralization step aqueous phase from step (a), said decomposition step aqueous phase from step (b) or both.

6. The process of claims 1 or 2 wherein said neutralization step aqueous phase is separated from said neutralized organic phase before said neutralized organic phase is treated in step (b).

7. The process of claim 6 wherein said separated neutralized organic phase is washed with water before being treated in step (b).

8. The process of claim 1 wherein the quantity of alkali metal hydroxide present in step (b) is such that the hydroxyl ion concentration in said decomposition step aqueous phase is 0.1 to 2 N.

9. The process of claim 8 wherein the hydroxyl ion concentration in said decomposition step aqueous phase is 0.6 to 1 N.

10. The process of claim 1 wherein said metal salt is a water-soluble transition metal salt, and is present in step (b) in a quantity of from 0.1 to 1,000 ppm by weight, calculated as metal relative to the weight of said decomposition step aqueous phase.

11. The process of claim 1 wherein the volume ratio between said decomposition step aqueous phase and said organic phase in said decomposition step (b) is at least 0.02.

12. The process of claim 11 wherein said volume ratio is between 0.05 and 0.20.

* * * * *